(12) United States Patent
Hildebrand et al.

(10) Patent No.: US 7,169,812 B2
(45) Date of Patent: Jan. 30, 2007

(54) PROCESS FOR PRODUCING INJECTABLE GABAPENTIN COMPOSITIONS

(75) Inventors: Keith R. Hildebrand, Houlton, WI (US); Linda M. Page, Woodbury, MN (US); Deanna S. Lane, Columbia Heights, MN (US); Dennis D. Elsberry, Plymouth, MN (US); David A. Clarahan, Blaine, MN (US); Jayantha H. Ratnayake, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 140 days.

(21) Appl. No.: 10/808,113

(22) Filed: Mar. 24, 2004

(65) Prior Publication Data

US 2005/0004220 A1 Jan. 6, 2005

Related U.S. Application Data

(63) Continuation-in-part of application No. 10/611,459, filed on Jul. 1, 2003, now Pat. No. 6,969,383.

(60) Provisional application No. 60/513,682, filed on Oct. 23, 2003, provisional application No. 60/513,681, filed on Oct. 23, 2003.

(51) Int. Cl.
*A61K 31/195* (2006.01)
(52) U.S. Cl. .................................................. 514/561
(58) Field of Classification Search ................ 514/561
See application file for complete search history.

(56) References Cited

U.S. PATENT DOCUMENTS

| | | | | |
|---|---|---|---|---|
| 4,024,175 A | * | 5/1977 | Satzinger et al. | 560/122 |
| 4,960,931 A | * | 10/1990 | Butler et al. | 562/507 |
| 5,068,413 A | * | 11/1991 | Steiner et al. | 562/507 |
| 5,603,894 A | * | 2/1997 | Aikus et al. | 422/23 |
| 6,046,353 A | * | 4/2000 | Grote et al. | 558/442 |
| 6,054,482 A | * | 4/2000 | Augart et al. | 514/561 |
| 6,521,787 B1 | * | 2/2003 | Bosch Llado et al. | 562/507 |
| 6,528,682 B1 | * | 3/2003 | Bosch Llado et al. | 562/507 |
| 2002/0198261 A1 | * | 12/2002 | Kulkarni et al. | 514/561 |
| 2003/0092933 A1 | * | 5/2003 | Chen et al. | 562/507 |

FOREIGN PATENT DOCUMENTS

| WO | WO 98/28255 | | 7/1998 |
|---|---|---|---|
| WO | WO 00/57927 A1 | | 10/2000 |
| WO | WO 200158881 A1 | * | 8/2001 |
| WO | WO 02/100347 A2 | | 12/2002 |
| WO | WO 02/100347 A3 | | 12/2002 |
| WO | WO 03/061656 A1 | | 7/2003 |
| WO | WO 03/070237 A1 | | 8/2003 |

OTHER PUBLICATIONS

Lagreze et al., "The neuroprotective properties of gabapentin-lactam," *Graefe's Arch. Clin. Exp. Ophthalmol.*, 2001; 239(11):845-849.

Li et al., Database Medline/NLM, Bethesda, MD, "Moist-heat sterilization and the chemical stability of heat-labile parenteral solutions," Database Accession No. NLM15605602 abstract, 1 pg.

\* cited by examiner

*Primary Examiner*—Johann Richter
*Assistant Examiner*—David P. Stitzel
(74) *Attorney, Agent, or Firm*—Keith M. Campbell

(57) ABSTRACT

Injectable compositions containing gabapentin and processes for preparing sterile injectable compositions containing gabapentin are discussed. The process includes subjecting the compositions to heat. Heating results in increased production of gabapentin lactam, which has previously been shown to be toxic. Surprisingly, heated injectable compositions containing gabapentin are found to be non-toxic when administered intrathecally. Thus, heating for the purposes of sterilization or to assure sterility provides a viable option in the production of injectable compositions containing gabapentin.

29 Claims, No Drawings

PROCESS FOR PRODUCING INJECTABLE GABAPENTIN COMPOSITIONS

RELATED APPLICATIONS

This application is a continuation in part application of Ser. No. 10/611,459, entitled "A method for treating severe tinnitus", filed Jul. 1, 2003 now U.S. Pat. No. 6,969,383. This application claims priority to the above-referenced application and also claims priority to Provisional Application Ser. No. 60/513682, entitled "INJECTABLE GABAPENTIN COMPOSITIONS", filed Oct. 23, 2003, and Provisional Application Ser. No. 60/513681, entitled "INTRATHECAL GABAPENTIN FOR TREATMENT OF PAIN AND EPILEPSY", filed on Oct. 23, 2003. Each of the above-referenced applications is herein incorporated by reference in their entirety.

FIELD OF THE INVENTION

This application relates to injectable compositions and kits comprising gabapentin and to processes for producing the same.

BACKGROUND OF THE INVENTION

Gabapentin is a pharmacological agent that mimics the effects of GABA (γ-aminobutyric acid), but gabapentin does not appear to bind a GABA receptor (e.g., $GABA_A$ and $GABA_B$ receptors) or have an effect on GABA uptake. Gabapentin has been found to interact with the alpha-2-delta ($β_2δ$) subunit of voltage-gated calcium channels. Many of the pharmacological effects of gabapentin may be due to its interaction with voltage-gated calcium channels. It is believed that gabapentin decreases calcium ion flow into a neuron, rendering the neuron less excitable. Inhibition of presynaptic calcium influx may prevent the release of neurotransmitters. Thus, like GABA, gabapentin can dampen overactive neural circuitry.

Solid formulations of gabapentin, such as NEURONTIN, are currently available for oral administration. Oral gabapentin has been used primarily to treat epilepsy although it has been used off-label to treat neuropathic pain and has recently received an FDA-approval for the treatment of one type of neuropathic pain, post-herpetic neuralgia. Some gabapentin can access the CNS when administered orally, because gabapentin is transported across the gut and the blood-brain barrier. It is believed that gabapentin is transported across the blood-brain barrier via an active and saturable L-amino acid transporter. Thus, the amount of gabapentin reaching CNS sites of action is limited. Because this transporter is saturable, even if the concentration of gabapentin in the plasma is increased, the amount which crosses the blood-brain barrier will remain constant.

Solutions of gabapentin have been prepared extemporaneously for direct administration to the CNS in preclinical animal studies. In some studies, such solutions have been administered intrathecally as a single bolus or as multiple boluses. However, the administration of a solution to the CNS presents many concerns, including the threat of serious infection. While such concerns are not of considerable importance in preclinical animal studies, they are of paramount importance in the context of administration to humans.

Accordingly, the sterility of a solution comprising gabapentin, which solution is to be administered to the CNS, cannot be taken lightly. Typically, solutions are sterilized either by heat or filtration. In the case of solutions containing gabapentin, a sterilization process involving heat would generally be considered undesirable. This is because heat would be expected to result in decreased stability of gabapentin and increased production of gabapentin lactam, having a chemical structure of formula (I):

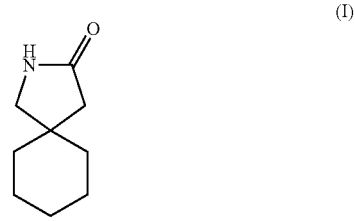

(I)

According to U.S. Pat. No. 6,054,482, "The lactams display a certain toxicity and must, therefore, be avoided as far as possible. For example, gabapentin has a toxicity ($LD_{50}$, mouse) of more than 8000 mg/kg, for the corresponding lactam (VI) a toxicity of 300 mg/kg." Column 4, lines 50–53. As a sterilization process involving heat may result in increased levels of the gabapentin lactam, heating of solutions prior to administration to the CNS of a patient would have been inadvisable.

SUMMARY OF THE INVENTION

An embodiment of the invention provides a process for preparing a pharmaceutical injectable compostion comprising gabapentin. The process comprises heating the injectable composition. Surprisingly, the inventors found that heating injectable compositions comprising gabapentin do not cause excessive toxicity when introduced into the CNS.

Heating of injectable compositions comprising gabapentin as part of a sterilization process provides several advantages. For example, using heat as form of terminal sterilization allows for sterilization of large quantities of composition(s) comprising gabapentin in an efficient manner. In addition, heat treatment following filter sterilization allows for added assurance that a composition comprising gabapentin is sterilized to a desired $F_0$ for administration to the CNS or other regions of a patient. These and other advantages of the invention will become evident upon reading the description herein.

DETAILED DESCRIPTION

The following description illustrates various embodiments of the invention. It is to be understood that other embodiments of the present invention are contemplated and may be made without departing from the scope or spirit of the present invention. Thus, the following description is not to be taken in a limiting sense.

All scientific and technical terms used in this application have meanings commonly used in the art unless otherwise specified. The definitions provided herein are to facilitate understanding of certain terms used frequently herein and are not meant to limit the scope of the present disclosure.

In the context of the present invention, the terms "treat", "therapy", and the like, as such terms refer to a disease, are meant to include methods to alleviate, slow the progression, prevent, attenuate, or cure the targeted disease.

As used herein, a heated injectable composition refers to a composition that has been heated at some point. It will be understood that a heated injectable composition may be essentially at room temperature, or any other desired temperature, prior to being injected into a subject.

As used herein, "injectable pharmaceutical composition" means a composition that may be infused or injected into a subject, which composition comprises a pharmaceutically active agent and is sterile to a $F_0$, or equivalent, suitable for administering to a human patient via injection or infusion.

Embodiments of the present invention provide injectable compositions comprising gabapentin. Injectable compositions comprising gabapentin according to embodiments of the invention may be used for any purpose for which study or use of gabapentin is desired. For example, injectable compositions comprising gabapentin may be used in studies to determine or elucidate (a) the effect of gabapentin on a molecule, cell, tissue, organ, organism, or combination thereof; (b) the mechanism of action of gabapentin, (c) the properties of gabapentin, a solution comprising gabapentin, or a combination thereof, and (d) the like. Injectable compositions comprising gabapentin may also be used as therapy to treat a disease or disorder responsive to gabapentin such as epilepsy, pain, tinnitus, drug addiction, bipolar disorder, osteoarthritis, migraine, and anxiety disorders including social phobia.

Injectable Composition

An embodiment of the invention provides an injectable composition comprising gabapentin. As used herein, gabapentin refers to 1-(aminomethyl)cyclohexane acetic acid and pharmaceutically acceptable salts, solvates, hydrates, and polymorphs thereof. 1-(aminomethyl)cyclohexane acetic acid is a γ-aminobutyric acid (GABA) analogue with a molecular formula of $C_9H_{17}NO_2$ and a molecular weight of 171.24. 1-(aminomethyl)cyclohexane acetic acid is freely soluble in water and both in basic and acidic aqueous solutions. 1-(aminomethyl)cyclohexane acetic acid has the following structure:

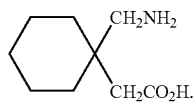

Gabapentin may be obtained from a variety of commercial sources, such as Shanghai Zhongxi International Trading Co., Shanghai, China; Hikal Limited, Bangalore, Karnaraka, India; Erregierre S.p.A., San Paolo d' Argon (BG), Italy; MediChem, SA, Sant Joan Despi (Barcelona), Spain; Ranbaxy Laboratories, New Delhi, India; Procos S.p.A., Cameri, Italy; Zambon Group, Milan, Italy; Hangzhuo Chiral Medicine Chemicals Co., Hangzhuo, China; InterChem Corporation USA, Paramus, N.J.; SST Corporation, Clifton, N.J.; Teva Pharmaceuticals USA, North Whales, Pa.; Plantex USA, Hakensack, N.J.; and Sigma-Aldrich, St. Louis, Mo., or an appropriate distributor. Alternatively, gabapentin may be synthesized and/or prepared as known in the art.

Injectable compositions include solutions, suspensions, dispersions, and the like. Injectable solutions, suspensions, or dispersions may be formulated according to techniques well-known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid.

Injectable compositions comprising gabapentin may be prepared in water, saline, isotonic saline, phosphate-buffered saline, citrate-buffered saline, and the like and may optionally mixed with a nontoxic surfactant. Dispersions may also be prepared in glycerol, liquid polyethylene, glycols, DNA, vegetable oils, triacetin, and the like and mixtures thereof. Under ordinary conditions of storage and use, these preparations may contain a preservative to prevent the growth of microorganisms. Pharmaceutical dosage forms suitable for injection or infusion include sterile, aqueous solutions, suspensions, or dispersions or sterile powders comprising an active ingredient which powders are adapted for the extemporaneous preparation of sterile injectable or infusible solutions or dispersions. Preferably, the ultimate dosage form is a sterile fluid and stable under the conditions of manufacture and storage. A liquid carrier or vehicle of the solution, suspension or dispersion may be a diluent or solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. Proper fluidity of solutions, suspensions or dispersions may be maintained, for example, by the formation of liposomes, by the maintenance of the desired particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin. Excipients that increase solubility, such as cyclodextrin, may be added.

In an embodiment, an injectable composition comprising gabapentin is an injectable composition comprising an aqueous solvent. The solvent may be water or saline. The saline may be, e.g., 0.9% (w/v) sodium chloride or a solution where just enough sodium chloride is added to make the final injectable composition isotonic. The saline may be sterile saline.

Any concentration of gabapentin may be present in an injectable composition according to various embodiments of the invention. For example, gabapentin may be present in a solution, suspension, or dispersion at a concentration between about 0.1 mg/mL and about 100 mg/mL. In an embodiment, gabapentin is present in a solution, suspension, or dispersion at a concentration between about 10 mg/mL and about 90 mg/mL. In an embodiment, gabapentin is present in a solution, suspension, or dispersion at a concentration between about 20 mg/mL and about 80 mg/mL. In an embodiment, gabapentin is present in a solution, suspension, or dispersion at a concentration between about 30 mg/mL and about 100 mg/mL. In an embodiment, gabapentin is present in a solution, suspension, or dispersion at a concentration of about 80 mg/mL. In an embodiment, an injectable composition comprises between about 10 mg/ml and about 50 mg/ml gababentin. For example, the composition may comprise between about 20 mg/ml and 40 mg/ml, or about 30 mg/ml. An injectable composition comprising gabapentin according to an embodiment of the invention includes an amount of gabapentin effective to treat a disease responsive to gabapentin. In an embodiment, the amount of gabapentin is effective to treat a gabapentin-responsive disease when administered intrathecally.

In an embodiment of the invention, an injectable composition comprising gabapentin has a pH between about 4 and about 9, between about 5 and about 7, between about 5.5 and about 6.5, or about 6. The pH of an injectable gabapentin composition may be adjusted with a pharmacologically acceptable acid, base, buffer or combination thereof. In an embodiment, pH is adjusted with hydrochloric acid or sodium hydroxide. The hydrochloric acid or sodium hydroxide may be in any suitable form, such as a 1N solution.

In an embodiment, the invention provides an injectable composition comprising gabapentin, where the composition is substantially isotonic with a physiological fluid of a subject. For example, the injectable solution may be isotonic with a subject's blood or cerebrospinal fluid. Cerebrospinal fluid typically has a tonicity of about 305 mOsm. Accordingly, an embodiment of the invention provides an injectable gabapentin composition having a tonicity of about 290 mOsm to about 320 mOsm. If an injectable composition comprising gabapentin has a tonicity lower than about 290 mOsm to about 320 mOsm, the tonicity may be enhanced by adding a tonicity enhancing agent, such as sodium chloride. As used herein, "tonicity enhancing agent" means a compound or composition that increases tonicity of a composition. However, such tonicities of between about 290 mOsm to about 320 mOsm are not always achievable with gabapentin compositions. For example, gabapentin dissolved in water at a concentration of 80 mg/ml has a tonicity of about 500 mOsm. When the concentration of gabaentin in an injectable composition renders the composition hypertonic relative to a subject's physiological fluid, it is preferred that little or no amount of a tonicity enhancing agent be added to the composition. However, it will be recognized that it may desirable to add one or more additional compounds to the composition even though the addition of the additional compound(s) will further increase tonicity of an injectable gabapentin solution. For example, it may be desirable to add to the composition an additional therapeutic agent, stabilizing compound, preservative, solubilizing agent, buffer, etc., even though tonicity will be increased.

In an embodiment of the invention, an injectable gabapentin composition is substantially free of preservatives, substantially free of buffers, or substantially free of both preservatives and buffers.

Sterile injectable composition comprising gabapentin may be prepared by incorporating gabapentin in the desired amount in the appropriate diluent or solvent with various other ingredients as enumerated above and, as desired, followed by sterilization. Any means for sterilization may be used. For example, sterilization may be accomplished by heating, filtering, aseptic technique, and the like, or a combination thereof. Heat for the purposes of sterilization may be heat for terminal sterilization or may be heat treatment associated with filtering and/or aseptic technique to accomplish the desired level of sterilization. In an embodiment, heating may be accomplished by autoclaving. As used herein "autoclave", "autoclaving", "autoclaved", and the like is a type of heating. Autoclaving is typically performed at 121.1° C. and 15 psig. In some circumstances it may be desirable to obtain a sterile powder for the preparation of sterile injectable solutions. Such sterile powders may be prepared by vacuum drying and freeze-drying techniques, which yield a powder of the active ingredient plus any additional desired ingredient present in a previously sterile-filtered solutions.

Heating as a Part of or to Accomplish Sterilization

In an embodiment of the invention, an injectable compositions comprising gabapentin is heated. Heating may serve to sterilize an injectable composition or may serve to assure sterility of an aseptically prepared injectable composition. Because increased temperature may result in increased conversion of gabapentin to its corresponding lactam, which is generally considered more toxic than gabapentin, it would be expected that high temperatures should be avoided when preparing compositions comprising gabapentin. Surprisingly, compositions comprising gabapentin may be heat treated or sterilized by autoclaving to provide suitable sterile injectable gabapentin compositions. Heating, whether or not through autoclaving, may be performed at any combination of temperature and time to sterilize a composition comprising gabapentin or assure sterility of an aseptically prepared composition. Heating may alone be sufficient to sterilize an injectable composition. Alternatively, heat treatment may be performed in conjunction with another form of sterilization and/or aseptic technique. For example, heat treatment may follow filtering. An injectable gabapentin composition may be filtered through any filter capable of enhancing sterility of the composition. For example, an injectable composition comprising gabapentin may be filtered through a filter having a pore size of about a 0.2 μm or about 0.22 μm. By way of non-limiting example, a composition may be subjected to heat of greater than or equal to about 105° C. In a further example, a composition may be subjected to heat for greater than or equal to about 2 minutes at a temperature of greater than or equal to about 105° C. In further examples, an injectable composition comprising gabapentin may be subjected to heat for about 2 minutes to about 60 minutes at temperatures of about 105° C. to about 140° C., for about 24 minutes at about 121° C., for about 4 minutes at about 130° C., for between about 6 minutes to about 8 minutes at about 121° C. In an embodiment, heating is performed at a temperature of about 121° C. It will be recognized that with higher temperatures and longer durations of application of heat, the likelihood of gabapentin lactam formation will be increased. To prevent excess formation of lactam, the time and temperature of heat application may be adjusted to a combination that reduces lactam formation, yet continues to provide a sterile injectable composition comprising gabapentin. To achieve the appropriate level of sterilization, heat may be applied in addition to filtering and/or aseptic technique.

In various embodiments of the invention, a heated injectable composition comprising gabapentin further comprises less than or equal to about 10% gabapentin lactam (formula I), less than or equal to about 5% gabapentin lactam, less than or equal to about 3% gabapentin lactam, less than or equal to about 2% gabapentin lactam, or less than or equal to about 1% gabapentin lactam. A heated injectable composition comprising gabapentin may also further comprise between about 0.5% and about 10% gabapentin lactam, between about 0.5% and about 5% gabapentin lactam, between about 0.5% and about 3% gabapentin lactam, between about 0.5% and about 2% gabapentin lactam, or between about 0.5% and about 1% gabapentin lactam. The above lactam levels are suitable for injection into the CNS of a subject and thus are suitable for pharmaceutical compositions. It will be recognized that gabapentin lactam formation and other degradation products may form during heating. As such, additional gabapentin may be added prior to heating the composition to compensate for degradation. For example, if an injectable composition comprising 80 mg/ml gabapentin is desired and if it is know that about 3% of the gabapentin degrades during heating, then 80 mg/ml plus and additional 3% may be present in the injectable composition prior to heating.

In various embodiments of the invention, an injectable composition comprising gabapentin is heated at an $F_0$ of about 1 or greater, about 2 or greater, about 3 or greater, about 4 or greater, about 5 or greater, about 6 or greater, about 7 or greater, about 8 or greater, about 9 or greater, about 10 or greater, about 12 or greater, about 18 or greater, or about 24 or greater. $F_0$ is a measure of efficiency of a specific heat sterilization process, which uses time in minutes at 121° C. as a reference. For example, a heat sterilization process that destroys organisms to the same extent as 8 minutes at 121° C. would have an $F_0$ of 8. In other words, $F_0$ is the equivalent time at 121° C. delivered to a container for the purposes of sterilization. Conversions to $F_0$ are within the ability of one of skill in the art and may be performed as described in Microbiology and Engineering of Sterilization Processes, seventh edition 1990, Irving J. Pflug, Parenteral Drug Association, Inc Technical Monograph 1 "Microbiology and Engineering of Sterilization Processes" reprinted 2000, which references are hereby incorporated herein by reference in their entirety.

In an embodiment, the invention provides a process for preparing an injectable composition comprising gabapentin. The composition may be a composition suitable for pharmaceutical use. The process comprises preparing an injectable composition comprising gabapentin and heating the composition to sterilize the composition or to assure the sterility of the composition. An injectable composition may be prepared as having properties described above. In an embodiment, gabapentin in a solid form, e.g. a dry powder, is added to a diluent or solvent to form an injectable composition. Additional excipients may be added. The injectable composition may be sterilized by, e.g., heating, filter sterilization, and the like or combinations thereof. The sterilized composition may be placed in a container. In an embodiment of the invention, the sterilized composition is placed in the container in an aseptic manner. The container may be any container capable of housing an injectable composition. Preferably the container is compatible with the injectable composition. In an embodiment, the container is a vial, ampule, or the like. The vial, ampule, etc. may be septum stoppered and capped with a flip-off seal. The composition may be terminally heat sterilized by heating a container housing the composition.

Administration

Injectable compositions, which have been subjected to heat, according to the invention may be administered to a subject through any pharmacologically acceptable route. For example, the compositions may be administered intravenously, subcutaneously, intramuscularly, intra-arterially, intra-articularly, inthrathecally, epidurally, intraparenchymally, intraperitoneally, intracerebroventricularly, etc., by infusion or injection.

In an embodiment of the invention, an injectable composition comprising gabapentin is adapted for intrathecal administration. Intrathecal administration of gabapentin provides a means for achieving effective spinal concentrations of gabapentin by bypassing the saturable L-amino acid active transport system and blood-brain barrier, while reducing concomitant systemic or supraspinal drug levels. Any effective amount of gabapentin may be administered intrathecally. For example, gabapentin may be administered intrathecally in a daily dose of between about 0.1 mg and about 200 mg. It will be understood that daily dose requirements may be adjusted to account for variability in CSF volume, CSF production rates, and rate of clearance of gabapentin from the CSF. One of skill in the art will understand that such variability may be due in part to, e.g., gender and/or age.

The following patent applications are generally relevant to injectable gabapentin and its use:

U.S. patent application Ser. No. 10/807,828, entitled INTRATHECAL GABAPENTIN FOR TREATMENT OF PAIN, filed on even date herewith;

U.S. patent application Ser. No. 10/808,129, entitled INJECTABLE GABAPENTIN COMPOSITIONS, filed on even date herewith;

U.S. patent application Ser. No. 10/807,827, entitled INTRATHECAL GABAPENTIN FOR TREATMENT OF EPILEPSY, filed on even date herewith; and U.S. patent application Ser. No. 10/808,054, entitled PUMP SYSTEMS INCLUDING INJECTABLE GABAPENTIN COMPOSITIONS, filed on even date herewith.

All patents, patent applications, technical papers, and other publications cited herein are hereby incorporated by reference herein, each in its respective entirety. As those of ordinary skill in the art will readily appreciate upon reading the description herein, at least some of the compositions, devices and methods disclosed in the patents and publications cited herein may be modified advantageously in accordance with the teachings of the present invention.

EXAMPLES

The following examples are provided to illustrate specific embodiments of the invention, and should not be construed as limiting the scope of the invention.

Example 1

Stability of Injectable Gabapentin Compositions Subjected to Heating

Gabapentin was dissolved in sterile water for injection, USP (lot 1), 50 mM sodium phosphate (lot 2), or 50 mM sodium citrate (lot 3) at a concentration of 80 mg/ml. The pH of the resulting solutions were adjusted to 6.0±0.2 with 1N NaOH and/or 1N HCl. 4.5 ml of the resulting pH-adjusted solutions were placed in 3.5 ml vials and subjected to autoclaving. Autoclaving occurred at 121° C. and 15 psig for 12 min. ($F_0$=12), 18 min ($F_0$=18), and 24 min ($F_0$=24). Gabapentin and gabapentin lactam concentrations of the autoclaved solutions were determined by HPLC. The results are presented in Table 1.

TABLE 1

Degradation of injectable gabapentin compositions by heating

| Lot | $F_0$ | Gabapentin (% Target Level)* | % Gabapentin Lactam (w/v) |
|---|---|---|---|
| 1 | 12 | 98.2 | 1.54 |
| 1 | 18 | 97.6 | 2.12 |
| 1 | 24 | 97.0 | 2.81 |
| 2 | 12 | 97.4 | 2.80 |
| 2 | 18 | 96.8 | 3.84 |
| 2 | 24 | 96.0 | 4.93 |
| 3 | 12 | 99.1 | 2.87 |
| 3 | 18 | 97.2 | 3.84 |
| 3 | 24 | 95.8 | 5.06 |

*% target level = [gabapentin concentration/(80 mg/ml)] × 100

Example 2

Heated Injectable Gabapentin Compositions are not Toxic

Rats were infused intrathecally with solutions containing varying concentrations of gabapentin. The solutions were subjected to heat prior to administration, and no toxic effects attributable to the infused solutions were observed.

Materials and Methods

Injectable solutions containing 80 mg/ml gabapentin were prepared and sterilized by heating to $F_0=24$ as described in Example 1. The heat-sterilized 80 mg/ml gabapentin solutions were diluted in sterile water for injection, USP (Abbott Laboratories; North Chicago, Ill.) to prepare solutions at gabapentin concentrations of 1.67, 4.17, and 37.5 mg/ml as shown in Table 2.

TABLE 2

Dilution of gabapentin solutions

| Group | Desired Conc. (mg/ml) | Volume of Gabapentin (ml)* | Volume of Vehicle (ml)* |
|---|---|---|---|
| 1 (Control) | 0 | 0 | 40.0 |
| 2 (Low) | 1.67 | 0.84 | 39.16 |
| 3 (Mid) | 4.17 | 2.09 | 37.91 |
| 4 (High) | 80.0 | 40.0 | 0 |
| 5 (Mid-High) | 37.5 | 18.75 | 21.25 |
| 6 (Control) | 0 | 0 | 40.0 |

*Volume of gabapentin (80 mg/ml) and vehicle (sterile water for injection, USP) needed to make 40 ml.

Osmotic minipumps (ALZET® Model 2ML4) were filled with approximately 2 ml of sterile water for Groups 1 and 6 or approximately 2 ml of the appropriate test article preparation for Groups 2 through 5. All dose preparations were filtered using a 0.22 µm filter prior to filling the osmotic minipumps.

Male and female Crl:CD®(SD)IGS BR rats were assigned to groups according to the study design shown in Table 3. The animals were obtained from Charles River Laboratories; Raleigh, N.C.. The animals were cannulated by the supplier in the intrathecal space overlying the lumbar vertebrae. The cannulae consisted of 1.3 cm PE-10 tubing attached to a 7 cm piece of polyurethane tubing (0.025 ID×0.040 OD) with a total dead volume of approximately 23.5 µl. On Day 1 (staggered based on sex), the animals were anesthetized and one prefilled osmotic pump/animal was aseptically inserted subcutaneously on the animal's dorsum. The cannula was filled with sterile water or test article preparation, as appropriate, and the pumps were connected to the intrathecal cannulae. Beginning on Day 1, animals were dosed 24 hours/day at a dose volume of approximately 60.96 µl/day via intrathecal infusion using the osmotic minipump through necropsy on Day 29. At initiation of dosing, the animals were 8 to 9 weeks old, and their body weights ranged from 264 g to 340 g for the males and 191 g to 264 g for the females.

TABLE 3

Study design and assignment of animals

| Group | No. of Animals Male | No. of Animals Female | Dose Level (mg/day) | Dose Concentration (mg/ml) | Approx. human dose equivalent (mg/day) |
|---|---|---|---|---|---|
| 1 (Control) | 5 | 5 | 0 | 0 | 0 |
| 2 (Low) | 5 | 5 | 0.10 | 1.67 | 8 |
| 3 (Mid) | 5 | 5 | 0.25 | 4.17 | 20 |
| 4 (High) | 5 | 5 | 4.8 | 80.0 | 384 |
| 5 (Mid-High) | 5 | 5 | 2.25 | 37.5 | 180 |
| 6 (Control) | 3 | 3 | 0 | 0 | 0 |

Assessment of toxicity was based on mortality, clinical observations, ophthalmic examinations, body weights, food consumption, clinical pathology, and anatomic pathology. Ophthalmic examinations were performed prior to initiation of treatment and during week 4. An indirect ophthalmoscopy examination was done to include, but was not limited to, a cursory examination of the adnexa and anterior structures of the globe (e.g., cornea, anterior chamber, lens) and a detailed examination of the ocular fundus. Body weights were taken prior to treatment, on Day 1, and weekly thereafter. Food consumption was measured weekly. At scheduled sacrifices, samples were taken for hematology, coagulation, and clinical chemistry. When possible, blood was collected from animals sacrificed at an unscheduled interval. Tissues were taken from each animal in groups 1 and 4 and each animal sacrificed at an unscheduled interval. Spinal cords were harvested from each animal in Groups 2, 3, and 5. The tissues and spinal cords were processed and examined microscopically. Macroscopic lesions were processed and examined microscopically from animals in Groups 2, 3, and 5. Sections of spinal cord from each animal in Groups 1 and 4 were embedded in paraffin, sectioned, and stained with luxol fast blue, and examined microscopically. Immunohistochemistry of spinal cord sections in paraffin from each animal in Groups 1 and 4 were sectioned, stained with anti-glial acidic fibrillary protein (Dako; Carpinteria, Calif.); rabbit IgG from Vector Laboratories; Burlingame, Calif. was used as a negative control), and examined.

The following hematology tests were performed: red blood cell (erythrocyte) count, hemoglobin, hematocrit, mean corpuscular volume, mean corpuscular hemoglobin concentration, platelet count, white blood cell (leukocyte) count, and differential blood cell count. The following coagulation tests were performed: prothrombin time and activated partial thromboplastin time. Clinical chemistry data was obtained on the following: glucose, urea nitrogen, creatinine, total protein, albumin, globulin, albumin/globulin ratio, cholesterol, triglycerides, total bilirubin, alanine aminotransferase, alkaline phosphatase, gamma glutamyl transferase, asparate aminotransferase, calcium, inorganic phosphorous, sodium, potassium, and chloride. The following tissues were weighed and harvested at sacrifice: adrenal, brain, epididymis, heart, kidney, liver, lung, ovary, pituitary gland, prostate, salivary gland (mandibular), seminal vesicle, spleen, testis, thymus, thyroid with parathyroid, and uterus. Paired organs; e.g., adrenal, epididymis, kidney, ovary, etc., were weighed together. Organ-to-body weight percentages and organ-to-brain weight ratios were calculated. The following tissues were preserved in 10%-neutral-buffered-formalin: adrenal, brain, cecum, colon, duodenum, epididymis, esophagus, eye, femur with bone marrow (articular surface of the distal end), Harderian gland, heart, ileum, infusion and catheterization sites and pumps, jejunum, kidney, lacrimal gland (exorbital), lesions, liver, lung with mainstem bronchi, lymph node (mesenteric), mammary gland (females), optic nerve, ovary, pancreas, pituitary gland, prostate, rectum, salivary gland (mandibular), sciatic nerve, seminal vesicle, skeletal muscle, skin, spinal cord (cervical, thoracic and lumbar), spleen, sternum with bone marrow, stomach, testis, thymus, thyroid with parathyroid, tongue, trachea, urinary bladder, uterus, and vagina.

Statistical analysis was performed as follows. Levene's test was done to test for variance homogeneity. In the case of heterogeneity of variance at $p \leq 0.05$, transformations were used to stabilize the variance. One way analysis of variance (ANOVA) was used where applicable to analyze continuous clinical pathology values, organ weight data, food consumption, and body weight data. When significant, Dunnett's t-test was performed for pairwise comparisons between treated and control groups. If ANOVA showed significance for body weights at Week 1, one-way analysis of covariance (ANCOVA) was used to analyze body weights, with initial body weights as the covariate. If the ANCOVA was significant, covariate-adjusted means were used for control versus treated group comparisons. Group comparisons (Groups 2–5 versus Group 1) were evaluated at the 5.0% two-tailed probability level. Only data collected on or after the first day of treatment was analyzed statistically. Evaluation of Group 6 data was limited to calculation of mean and standard deviation.

Results

Insignificant or incidental differences between treated groups (Groups 2–5) and control Group 1 were observed.

1. Observations

On Day 11, one male given 4.8 mg/day was observed with limited use of its hind limbs, the osmotic pump was exposed, and the catheter did not appear to be connected; the animal was sacrificed in moribund condition. On Day 17, one male given 2.25 mg/day was observed with limited use of its hind limbs; the animal was sacrificed in moribund condition. On Days 20 and 21, one female given sterile water (Group 6) was observed with black skin on the right ventral abdominal region and a sore/scab on the right lateral abdominal region; the animal was sacrificed on Day 21. All of these unscheduled deaths were attributed to complications secondary to the intrathecal infusion system. All other animals survived to scheduled sacrifice.

Animals that survived to the scheduled sacrifice had no significant observations related to test article administration. A number of clinical observations were made, but these did not show any dose relations and were considered incidental.

One female given 0.1 mg/day (Group 2) and one female given 4.8 mg/day (Group 4, left eye) were observed to have an opaque eye. Upon further examination, these two individual animals were confirmed to have corneal keratitis in the affected eye. One male given 4.8 mg/day (Group 4, left eye) was diagnosed with corneal keratitis and one female given 2.25 mg/day (Group 5, left eye) with corneal ulceration. These few noted incidences of corneal keratitis and one noted incidence of corneal ulceration were considered an artifact of surgical procedures but not related to test article administration.

Females given 2.25 mg/day (Group 5) had significantly lower body weights for Weeks 1 to 3 as compared to Group 1 controls, but the lower mean body weight did not appear to be different from the concurrent controls (Group 6) and this was considered incidental as the Group 5 animals had lower body weights at initiation compared to animals in Group 1. There were no clear test article-related effects on mean body weights, body weight changes, or food consumption.

2. Clinical and Anatomic Pathology

Administration of intrathecal gabapentin, terminally sterilized by heat, had no obvious or adverse effect on clinical pathology test results. The only statistically significant differences for clinical pathology test results between the control and treated animals (i.e., lower gamma glutamyl-transferase for males and females given 2.25 mg/day) were considered incidental, as animals given 4.8 mg/day were not similarly affected. The most prominent findings for three animals sacrificed at unscheduled intervals because of poor health, including a control female from Group 6, were increased absolute neutrophil count and globulin concentration and decreased albumin concentration. These findings were consistent with an inflammatory response and considered incidental because there was no relationship to dose and animals that survived to the scheduled sacrifice did not exhibit similar findings.

The catheter tip was located between L3 and L6 of the subarachnoid space in 48 animals; in 3 animals the catheter was epidural. There were no test article-related organ weight differences, macroscopic observations, or microscopic observations. Several observations were related to the infusion apparatus and catheter. In several animals, there was nerve degeneration in the nerve roots in the region of catheter placement. Often gliosis accompanied the degeneration. In the animals not surviving to the scheduled sacrifice, inflammatory processes, including abscess and pyogranulomas, were present at the infusion or catheter sites or surrounding the infusion pump.

There was no significant variation in glial fibrillary acidic protein immunostaining of spinal cord sections between the control and high-dose group animals.

Discussion

Despite elevated gabapentin lactam concentrations due to subjecting gabapentin compositions to heat, gabapentin delivered at dose levels of 0, 0.10, 0.25, 2.25, and 4.8 mg/day was well tolerated and non-toxic when administered intrathecally. No clear effects were observed on clinical observations, body weights, body weight changes, food consumption, ophthalmic observations, or clinical or anatomic pathology observations.

We claim:

1. A process for preparing an injectable pharmaceutical composition comprising gabapentin, the process comprising:
    preparing an injectable composition comprising gabapentin and a pharmaceutically acceptable vehicle; and
    heating the injectable composition at greater than or equal to about 105° C. to produce the injectable pharmaceutical composition.

2. The process of claim 1, wherein the heating sterilizes the composition.

3. The process of claim 1, further comprising filtering the injectable composition.

4. The process of claim 3, further comprising aseptically placing the filtered composition in a container to produce a container housing the filtered composition.

5. The process of claim 4, wherein the heating comprises heating the container housing the composition.

6. The process of claim 1, further comprising adjusting the pH of the injectable composition.

7. The process of claim 1, wherein the heating comprises autoclaving.

8. The process of claim 1, wherein the heating comprises heating the injectable composition at greater than or equal to about 105° C. for greater than or equal to about 2 minutes.

9. The process of claim 8, wherein the heating comprises heating the injectable composition at between about 105° C. and about 140° C. for between about 2 minutes and about 60 minutes.

10. The process of claim 9, wherein the heating comprises heating the injectable composition at greater than or equal to about 121° C. for about 24 minutes.

11. The process of claim 9, wherein the heating comprises heating the injectable composition at greater than or equal to about 130° C. for about 4 minutes.

12. The process of claim 9, wherein the heating comprises heating the injectable composition at greater than or equal to about 118° C. for between about 6 minutes to about 8 minutes.

13. The process of claim 1, wherein the injectable pharmaceutical composition comprises less than or equal to about 10% (w/v) gabapentin lactam.

14. The process of claim 13, wherein the injectable pharmaceutical compositioncomprises less than or equal to about 5% (w/v) gabapentin lactam.

15. The process of claim 14, wherein the injectable pharmaceutical composition comprises less than or equal to about 2% (w/v) gabapentin lactam.

16. The process of claim 15, wherein the injectable pharmaceutical composition comprises less than or equal to about 1% (w/v) gabapentin lactam.

17. The process of claim 1, wherein the injectable pharmaceutical composition comprises between about 0.5% (w/v) and about 10% (w/v) gabapentin lactam.

18. The process of claim 1, wherein the injectable pharmaceutical composition comprises between about 0.1 mg/ml and about 100 mg/ml gabapentin.

19. The process of claim 18, wherein the injectable pharmaceutical composition comprises between about 30 mg/ml to about 100 mg/ml gabapentin.

20. The process of claim 19, wherein the injectable pharmaceutical composition comprises about 80 mg/ml gabapentin.

21. The process of claim 1, wherein the injectable pharmaceutical composition comprises between about 10 mg/ml and about 50 mg/ml gabapentin.

22. The process of claim 1, wherein the injectable pharmaceutical composition comprises between about 20 mg/ml and about 40 mg/ml gabapentin.

23. The process of claim 1, wherein the injectable pharmaceutical composition comprises about 30 mg/gabapentin.

24. The process according to claim 6, wherein the pH is adjusted by adding sodium hydroxide, hydrochloric acid, or both to the injectable composition.

25. A process for preparing an injectable pharmaceutical composition comprising gabapentin, the process comprising:
   preparing an injectable composition comprising gabapentin and a pharmaceutically acceptable vehicle;
   adjusting the pH of the injectable composition;
   filtering the pH-adjusted injectable compostion;
   aseptically placing the filter-sterilized composition into a container; and
   heating the container housing the composition at greater than or equal to about 105° C. to produce the injectable pharmaceutical composition.

26. The process according to claim 25, wherein the injectable pharmaceutical composition is substantially free of preservatives and substantially free of buffers.

27. The process of claim 25, wherein the filtering comprises filtering the pH adjusted injectable composition through a filter having a pore size of about 0.22 μm.

28. The process of claim 25, wherein the process produces a composition having a level of sterility equivalent to a composition heated to an $F_0$ of about 8 or greater.

29. The process of claim 25, wherein the process produces a composition having a level of sterility equivalent to a composition heated to an $F_0$ of about 24 or greater.

* * * * *